United States Patent
Nuninger et al.

(12) 
(10) Patent No.: US 6,228,884 B1
(45) Date of Patent: May 8, 2001

(54) FUNGICIDAL COMPOSITION AND METHOD OF CONTROLLING FUNGUS INFESTATION

(75) Inventors: Cosima Nuninger, Morschwiller le Bas (FR); John Edward Nicholas Goggin, Binningen (CH); Dino Sozzi, Sissach (CH); Holm Ellgehausen, Magden (CH)

(73) Assignee: Syngenta Investment Corporation, Greensboro ( * ) Notice: Subject to any disclaimer, the term of this patent is extended or adjusted under 35 U.S.C. 154(b) by 0 days.

(21) Appl. No.: 09/174,704

(22) Filed: Oct. 19, 1998

Related U.S. Application Data

(60) Continuation of application No. 08/863,750, filed on May 27, 1997, which is a division of application No. 08/460,158, filed on Jun. 2, 1995, now Pat. No. 5,723,491.

(30) Foreign Application Priority Data

Jul. 11, 1994 (CH) .................................... 2207/94
Dec. 22, 1994 (CH) .................................... 3895/94

(51) Int. Cl.$^7$ .......................... A01N 37/12; C07C 229/02
(52) U.S. Cl. .......................... 514/538; 514/535; 514/536; 560/43
(58) Field of Search .................... 514/538, 535, 514/536; 560/43

(56) References Cited

U.S. PATENT DOCUMENTS 4,151,299  4/1979  Hubele .
5,723,491  *  3/1998  Nuninger et al. .

FOREIGN PATENT DOCUMENTS 1448810  9/1976  (GB) .

OTHER PUBLICATIONS

Fisher and Hayes, Crop Protection, 1985, 4 (4), pp. 501–510.
Gozzo et al., Pesticide Science, vol. 16, No. 3, Jun. 1985.
Schwinn et al., Abhandlungen dder Akademie der Wissenschaft der DDR, vol. 1982, No. 1, 123–133, (1983).
Moser, H.; Vogel, C; (1978). Preparation and Biological Activity of the Enantiomers of CGA48988, a New Systemic Fungicide. Fourth International Congress of Pesticide Chemistry (IUPAC), Zurich, Jul. 24–28, 1978. Abstract vol. II, p. 310.

* cited by examiner

*Primary Examiner*—Shailendra Kumar
(74) *Attorney, Agent, or Firm*—William A. Teoli, Jr.

(57) ABSTRACT

If the R-enantiomer of metalaxyl, furalaxyl or benalaxyl is used, this results in a markedly increased biodegradability of these plant fungicides in the soil and a higher activity on the plants, as compared with the data of the racemic active ingredients. Fungicidal compositions exhibiting said improved properties comprise either of these fungicides with a content of R-enantiomer of more than 70 percent by weight based on the total amount of active ingredient.

7 Claims, 2 Drawing Sheets

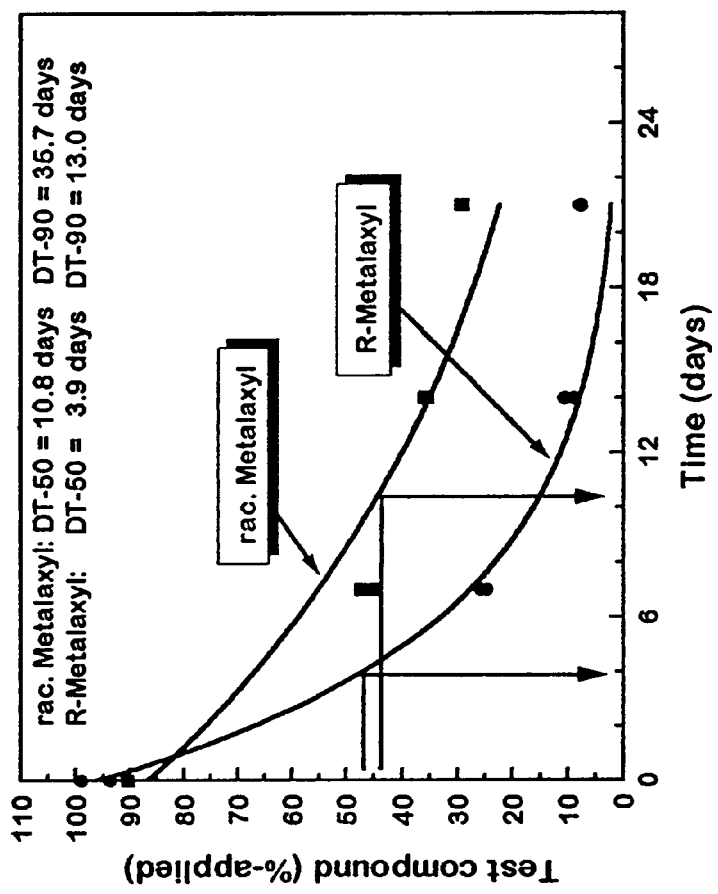
Figure 1: Rate of Degradation of rac. Metalaxyl and R-Metalaxyl in fieldfresh Soil (Silt-loam) under laboratory Conditions.
DT-50: Disappearance Time for 50 % a.i.(Time until 50% of the fungicide are degraded)
DT-90: Disappearance Time for 90 % a.i.(Time until 90% of the fungicide are degraded)

Figure 2: Rate of Degradation of rac. Metalaxyl and R-Metalaxyl in fieldfresh Soil (Sand) under laboratory Conditions.
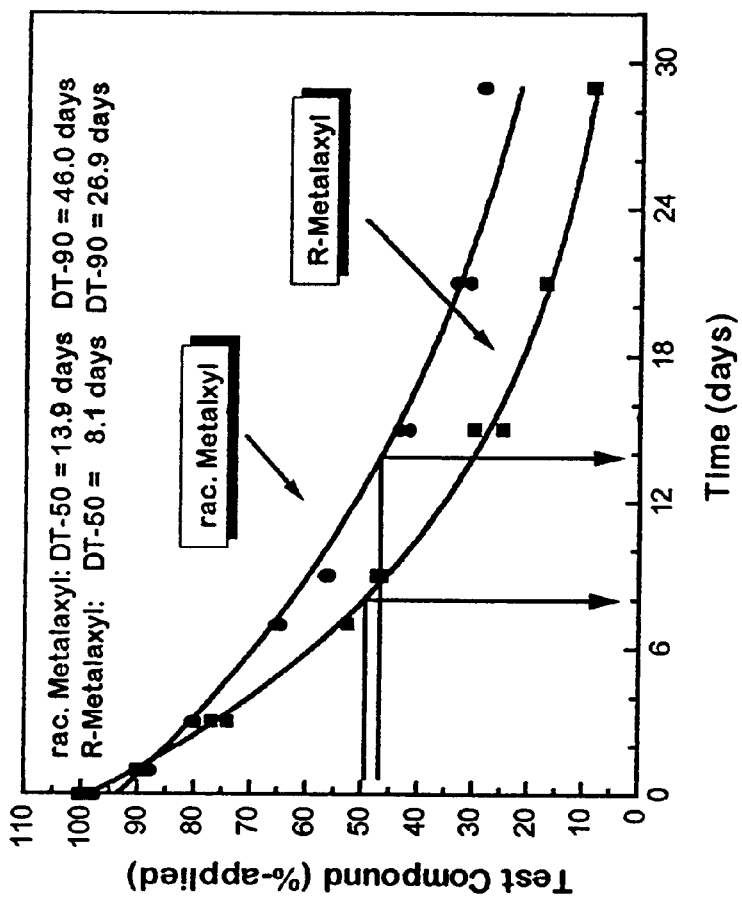
DT-50: Disappearance Time for 50 % a.i.(Time until 50% of the fungicide are degraded)
DT-90: Disappearance Time for 90 % a.i.(Time until 90% of the fungicide are degraded)

FUNGICIDAL COMPOSITION AND METHOD OF CONTROLLING FUNGUS INFESTATION

This application is a continuation of application Ser. No. 08/863,750 filed on May 27, 1997, now abandoned, which is a divisional of application Ser. No. 08/460,158 Jun. 2, 1995, now U.S. Pat. No. 5,723,491.

The present invention relates to a novel method of controlling and preventing Oomycete infection of plants by using metalaxyl, furalaxyl or benalaxyl, hereinbelow termed active ingredient I, in each case with an R-enantiomer content of over 70% by weight, and to suitable fungicidal compositions for this purpose.

Metalaxyl was the first commercially available preparation from the series of the class of active ingredients originally termed acylalanines, later phenylamides, which are outstandingly active against Oomycetes. The Oomycetes include all downy mildews, which attack mainly potatoes, tomatoes, vines, hops, maize, sugar beet, tobacco, vegetables, lettuce, but also bananas, rubber, as well as lawns and ornamentals.

The preferred application of the acylalanine fungicides is foliar application, the foliage and the growing plant being treated with the active ingredient. Some of the active ingredient is taken up by the plant, but some remains on the plant and is washed off by the rain or otherwise taken up by the soil due to leaf drop or time of maturation. In the case of soil application, the active ingredient is incorporated into the soil directly by applying it in liquid form, or, for example, by means of granules.

A disadvantage in this context is the slow degradation rate of the representatives of this substance class in the soil, which depends largely on whether the soils are humous soils, mixed sandy/loamy soils or strongly adsorptive soils (loam/clay). In the case of prolonged treatment periods, on the one hand in perennial crops, such as grapevines, on the other in typical soil crops, such as potatoes, sugar beet or lawns, the soils may be subjected to cumulative loading with acylalanine fungicides, which, in turn, are an environmental hazard, but in particular a groundwater hazard.

Metalaxyl is N-(2,6-dimethylphenyl)-N-(methoxyacetyl)-DL-alanine methyl ester.
Benalaxyl is N-(2,6-dimethylphenyl)-N-(phenylacetyl)-DL-alanine methyl ester.
Furalaxyl is N-(2,6dimethylphenyl)-N-(2-furanylcarbonyl)-DL-alanine methyl ester.

The compounds are known from the literature. The degradation data given vary. The reference book "The Pesticide Manual", 10th Edition 1994, edited by the British Crop Protection Council, gives the following information on the hydrolytic half-lives of these products. (DT=disappearance time).

| | |
|---|---|
| Metalaxyl: DT-50 (20° C.) | pH1: >200 d |
| | pH9: 115 d |
| Benalaxyl: DT-50 | pH9.25: 86 d |
| Furalaxyl: DT-50 (20° C.) | pH1: >200 d |
| | pH9: >200 d |

These data show an undesirably high stability in the aqueous medium.

Attempts were made to accelerate the degradation behaviour by means of suitable formulations, for example by means of hydrophobic additives which prevent deeper penetration of the active ingredient into the soil and expose it on the surface to the incidence of sunlight and to elevated temperatures. It was attempted to exploit a further disadvantageous property of the acylalanine fungicides, namely their high volatility, which is a nuisance under the effect of sun and high temperatures. It would have been expected that the volatility of the active ingredient on the soil surface would be equally high, a fact which has not been observed in practice.

All these attempts have not resulted in convincing solutions. Once the active ingredient is adsorbed by the soil surface, even only within the uppermost 2 cm, degradation is reduced drastically, which entails all the adverse consequences of sparingly degradable active ingredients which the expert is familiar with.

Entirely surprisingly, it has now been found that the solution of this problem is found in the acylalanine active ingredient itself, in which the R-enantiomer is, unexpectedly, degraded more rapidly than the S-enantiomer or than the commercially available active ingredients which are based on the racemates in question. Since 1975, which is when this substance class became known, one has been familiar with the fact that it is the R-enantiomer anyway which is the more fungicidally active ingredient (cf e.g. GB-1 500 581).

As a solution for practical use, the literature has never seriously proposed, in 19 years, the allegedly adjacent solution of using, from the start, the respective R-enantiomer of an acylalanine fungicide. On the one hand, one must not underestimate the technological difficulties of preparing an R-enantiomer in pure form or an active substance enriched with R-enantiomer (for example fractional crystallization of the racemate or stereospecific synthesis), on the other hand there was no incentive and no technological necessity for the practitioner for acting in such a way. However, the decisive factor is this. It could not have been assumed that a reduction or complete elimination of the proportion of S-enantiomer in the racemate would solve the problem of the unduly long residence time of the active ingredient in the soil. As yet, no R-enantiomers, or R-enantiomer-enriched racemates, of acylalanine fungicides have been put on the market. With respect to the overall ecological situation of the otherwise effective control of downy mildews (Oomycetes) with acylalanine fungicides, in particular with metalaxyl, the solution of the degradation problem proposed herein is of decisive technological importance in agricultural practice worldwide. It is a standard demand in crop protection to achieve an optimal effect with an active ingredient at the lowest dosage rate required while simultaneously keeping the pollution of the environment as low as possible.

In the field of the acylalanine fungicides, in particular in the case of its main representative, metalaxyl, this problem can be considered as solved. An evidently better biodegradability in the soil is achieved if the content of R-enantiomer in the active ingredient is over 70% by weight.

BRIEF DESCRIPTION OF THE DRAWINGS

FIG. 1 illustrates degradation curves that depict the rate of degradation of rac.metalaxyl and R-metalaxyl in fieldfresh soil(silt/loam) under laboratory conditions.

FIG. 2 illustrates degradation curves that depict the rate of degradation of rac. Metalaxyl and R-metalaxyl in fieldfresh soil(sand) under laboratory conditions.

The present invention provides an ecologically desirable method of controlling and preventing Oomycete infestation of plants by using an R-enantiomer of metalaxyl or benalaxyl

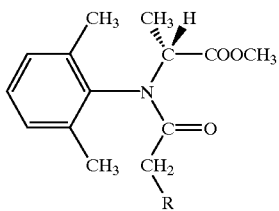

R=OCH₃ (R-metalaxyl)
R=C₆H₅ (R-benalaxyl)
or by using the R-enantiomer of furalaxyl

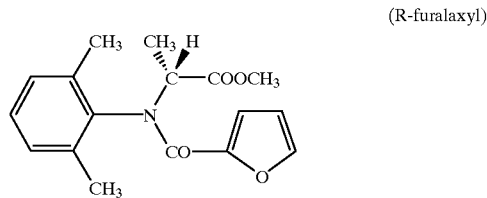
(R-furalaxyl)

in each case at least 70 percent by weight of the particular amount of total active ingredient.

Here and below, the racemates of the three active ingredients metalaxyl, benalaxyl and furalaxyl are termed active ingredient I. With increasing contents of R-enantiomer in the active ingredient the degradation properties in the soil are improved.

The invention preferably relates to a method of controlling Oomycetes in which the active ingredient employed has an R-enantiomer content of over 85% by weight, in particular over 92%, and preferably over 97%, based on the total amount of active ingredient. Particularly preferred is the method in which the active ingredient I is essentially composed of R-enantiomers and is essentially free of S-enantiomers (<1%).

The present invention furthermore relates to a composition for controlling Oomycetes in which the amount of R-enantiomers in active ingredient I amounts to over 70% by weight, preferably 85% by weight, and particularly prefered over 92%, based on the total amount of active ingredient In particular, the invention relates to a composition wherein the content of the R-enantiomer in the active ingredient is more than 97% by weight and especially to one wherein the active ingredient is essentially free from S-enantiomer (<1% by weight). The indicated percentages do not take into account that technically produced active ingredient additionally contains traces of by-products and intermediates (ca. 3–5% b.w.).

The composition and the method of the present invention control, amongst the Oomycetes, in particular fungal pests from the group of the Peronosporales, in particular *Plasmopara viticola*, furthermore Phytophthora spp., such as *P. infestans, Pythium pathogens,* Bremia, Pseudoperonospora and others.

The rates per application (spraying, dusting, incorporation into the soil and the like) are 60 g of active ingredient per hectare (a.i./ha) to 300 g of a.i./ha based on the pure R-enantiomer.

The active ingredient employed can be furalaxyl, benalaxyl, but preferably metalaxyl. Formulations of R-metalaxyl are preferably highly concentrated (more than 30% b.w. of active ingredient). This results in savings in transport and storage capacity.

Furthermore, pathogens on live plants have revealed that the activity displayed by the R-enantiomer of active ingredient I is many times higher in comparison with the racemate and not just twice as high, as expected. The activity can be 20 to 30 times higher, under certain conditions up to 100 times higher, than in the case of the racemate.

Conformation studies demonstrated that in the type of active ingredient in question of the acylalanines of the formula above, the right-hand side half of the molecule (see above) is fixed in a virtually vertical position relative to the 2,6-dimethylphenyl plane when in the crystalline state and that in solutions, when this barrier of rotation about the phenyl-N-axis can be overcome by energy, the methylene group to which the substituent R is attached forms an angle towards this phenyl group, as shown above by the formula (R. Nyfeler, P. Huxley, Monograph No. 31, British Crop Protection Conference Publication, Croydon 1985, p. 45 et seq.). This means that the remaining substituents in the molecule can vary their positions relative to the C atom of the alanine methyl ester, which is responsible for the absolute configuration. This also applies analogously to the compound furalaxyl, which has attached to it a 2-furanyl radical instead of the substituent CH₂—R, which is shown above.

In recent years, a plurality of biological investigations have confirmed, in principle, the finding that the R-enantiomer has a better fungicidal activity than the S-enantiomer. In Phytophthora palmivora, D. J. Fisher and A. L. Hayes (Crop protection [1985] 4 (4) pp. 501–510) found that the $ED_{50}$ inhibitory values in the nucleic acid synthesis were approximately fifty times more unfavorable in the case of the S-enantiomer of metalaxyl than in the case of the R-enantiomer, while the corresponding $ED_{50}$ values of R-enantiomer and racemate were in a ratio of approximately 3.1:5.6. The skilled man would thus expect that the activity of a given amount of R-enantiomer is approximately equivalent to twice the amount of racemate, and readily conclude that the much lower activity of the S-enantiomer in the racemate attributes, to this S-enantiomer, essentially the role of an inert material whose presence does not matter.

Resolution of the racemate of active ingredient I and use of the R-enantiomer only was therefore not an option for the practitioner, even if only because of the high level of action of the racemates, and has therefore not been proposed in the literature of the last 19 years as a solution for practical use.

Thus, it has to be assumed that, in the ready-for-use state of the racemic active ingredient I, the contribution of the R-enantiomer to the activity is reduced antagonistically by the S-enantiomer and by other conformations of the molecule. For example, it would be conceivable that a large number of biochemical receptors are temporarily occupied by the ineffective components of the racemate I, but not permanently blocked. Since, furthermore, the active ingredients I, in particular metalaxyl and furalaxyl, became known for having a systemic and penetrating action, further negative effects of these isomers, which have previously prevented the rapid penetration capacity of the R-enantiomer into the cell tissue of the plant and have resulted in elevated losses due to volatilization, might also play a role.

The R-enantiomers of the formula I can be obtained for example by fractional crystallization of a salt prepared from N-(2,6-dimethylphenyl)-α-aminopropionic acid and an N-containing optically active base with subsequent liberation of the optically active antipode and esterification with methanol. An example of an optically active base is α-phenylethylamine (GB P.1 448 810).

Furthermore, the R-enantiomers of the active ingredients can also be obtained by the activation of the hydroxyl group as leaving group in the naturally occurring L(+) lactic acid, esters or salts, and its replacement by 2,6-dimethylaniline with reversal of configuration. The use of the acid or its salts necessitates subsequent esterification with methanol. The use of an lactic ester other than the methylester necessitates subsequent transesterification with methanol. The boiling point of pure R-metalaxyl is 143–145° C./0.03 mbar.

The active ingredient in question is formulated in a known manner to give pesticidal compositions, as is described, for example, in GB P.1 500 581.

The formulations are prepared in a known manner, for example by intimately mixing and/or grinding the active ingredients with extenders, such as, for example, with solvents, solid carriers and, if appropriate, surface-active compounds (surfactants).

Suitable carriers and additives can be solid or liquid and correspond to the substances expediently used in formulation technology, such as, for example, natural or regenerated mineral substances, solvents, dispersants, wetting agents, tackifiers, thickeners, binders or fertilizers.

A preferred method of applying the R-enantiomer is application to the aerial parts of the plant, especially the foliage (foliar application). Number and rate of application depend on the biological and climatic environmental conditions for the pathogen. Alternatively, the R-enantiomer can reach the plant via the soil through the root system (systemic action), by drenching the site of the plant with a liquid composition or by incorporating the substances into the soil in solid form, for example in the form of granules (soil application).

The compound is employed as pure active ingredient or, preferably, together with the adjuvants conventionally used in the art of formulation and is therefore processed in a known manner to give, for example, emulsion concentrates, spreadable pastes, directly sprayable or dilutable solutions, dilute emulsions, wettable powders, soluble powders, dusts, granules, or by encapsulation, for example in polymeric substances. The methods of application, such as spraying, atomizing, dusting, scattering, brushing on or pouring, as well as the type of the compositions, are selected to suit the intended aims and the prevailing circumstances.

As a rule, the agrochemical compositions comprise 0.1 to 99%, in particular 0.1 to 95%, of active ingredient I, 99.9 to 1%, in particular 99.9 to 5%, of a solid or liquid additive, and 0 to 25%, in particular 0.1 to 25%, of a surfactant.

While concentrated compositions are more preferred as commercially available goods, the end consumer uses, as a rule, dilute compositions. Such (agro)chemical compositions are part of the present invention.

The examples which follow are intended to illustrate the invention, "active ingredient I" preferably being metalaxyl, but also furalaxyl or benalaxyl, with a preferably high R-enantiomer content (70–100% by weight).

| Wettable powders | a) | b) | c) | d) |
|---|---|---|---|---|
| Active ingredient metalaxyl (96% R-enantiomer) | 25% | 50% | 75% | 24% |
| Sodium lignosulfonate | 5% | 5% | — | 5% |
| Sodium lauryl sulfate | 3% | — | 5% | 4% |
| Sodium diisobutylnaphthalene-sulfonate | — | 6% | 10% | — |
| Octylphenol polyethylene glycol ether (7–8 mol of ethylene oxide) | — | 2% | — | — |

-continued

| Wettable powders | a) | b) | c) | d) |
|---|---|---|---|---|
| Highly-disperse silica | 5% | 10% | 10% | 5% |
| Kaolin | 62% | 27% | — | 62% |

The active ingredient is mixed thoroughly with the additives and the mixture is ground thoroughly in a suitable mill. This gives wettable powders which can be diluted with water to give suspensions of any desired concentration.

| Emulsion concentrate | |
|---|---|
| Active ingredient metalaxyl (96% R-enantiomer) | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired dilution, which can be employed in crop protection, can be prepared from this concentrate by diluting it with water.

| Dusts | a) | b) | c) |
|---|---|---|---|
| Active ingredient I (>85% R-enantiomer) | 5% | 6% | 4% |
| Talc | 95% | — | — |
| Kaolin | — | 94% | — |
| Rock powder | — | — | 96% |

Ready-for-use dusts are obtained by mixing the active ingredient with the carrier and grinding the mixture in a suitable mill.

| Extruder granules | |
|---|---|
| Active ingredient I (>92% R-enantiomer) | 15% |
| Sodium lignosulfonate | 2% |
| Carboxymethylcellulose | 1% |
| Kaolin | 82% |

The active ingredient is mixed with the additives, and the mixture is ground and moistened with water. This mixture is extruded and subsequently dried in a stream of air.

| Coated granules | |
|---|---|
| Active ingredient I (>70% R-enantiomer) | 8% |
| Polyethylene glycol (MW 200) | 3% |
| Kaolin | 89% |
| (MW = molecular weight) | |

In a mixer, the finely ground active ingredient is applied uniformly to the kaolin which has been moistened with polyethylene glycol. In this manner, dust-free coated granules are obtained.

| Suspension concentrate | |
|---|---|
| Active ingredient I (>92% R-enantiomer) | 40% |
| Propylene glycol | 10% |
| Nonylphenol polyethylene glycol ether (15 mol of ethylene oxide) | 6% |
| Sodium lignosulfonate | 10% |
| Carboxymethylcellulose | 1% |
| Silicone oil (in the form of a 75% aqueous emulsion) | 1% |
| Water | 32% |

The finely ground active ingredient is mixed intimately with the additives. This gives a suspension concentrate from which suspensions of any desired dilution can be prepared by diluting it with water. Such dilutions can be used for treating live plants and plant propagation material by spraying, watering or immersing and for protecting them against attack by microorganisms.

I) Biological Examples

Test Method

Vine plantlets cv. "Gutedel" are grown under greenhouse conditions using one plant per pot (Ø=6 cm) and sprayed with a spray broth prepared from an emulsion concentrate, either in the two-leaf stage or in the three-leaf stage. The following concentrations of active ingredient are used per batch of 4 plants: 200; 60; 20; 6; 2; 0.6; 0.2; 0.06 mg of a.i./liter. This dilution series is prepared in demineralized water immediately prior to application as a foliar spray. To exclude a gas-phase effect of the a.i. in the vicinity, all plants are separated from each other on the side using translucent plastic foils and kept in the dark for one day at 20–22° C. and a relative humidity of approximately 100%.

Then, the entire leaf surface area of the plants is uniformly sprayed to drip point with a freshly prepared sporangia suspension (120 000/ml) of a metalaxyl-sensitive strain of *Plasmopara viticola*. The plants are then kept for 7 days under a 16 hour photoperiod with artificial daylight at 20–22° C. and a relative humidity of approximately 100%. This is followed by evaluation of the infestation, separating three-leaf and two-leaf stage sprayings. The tables show in each case the average of 4 parallel sprayings.

A) Sprayings in the two-leaf stage (*Pl. viticola* on vines)

| Level of action of R-metalaxyl and racemic metalaxyl | | |
|---|---|---|
| Active ingredient | Dose [mg of a.i./litre] | Foliar infestation [%] |
| R-metalaxyl | 200 | 0 |
| | 60 | 0 |
| | 20 | 0 |
| | 6 | 0 |
| | 2 | 4 |
| | 0.6 | 78 |
| | 0.2 | 97 |
| | 0.06 | 92 |
| untreated control | | 96 |
| racemic metalaxyl | 200 | 0 |
| | 60 | 0 |
| | 20 | 38 |
| | 6 | 76 |
| | 2 | 87 |
| | 0.6 | 100 |
| | 0.2 | 97 |
| | 0.06 | 96 |

While conventional racemic metalaxyl does not result in a clear-cut action against foliar infestation in a concentration range of below 60 mg of a.i./liter and is without effect for practical purposes at a concentration of below 20 mg of a.i./liter, the activity of enantiomeric R-metalaxyl is up to 30 times better up to dilutions of 2 mg of a.i./liter.

In the case of spraying in the three-leaf stage, the differences in activity are even clearer, as shown by Table B).

B) Sprayings in the three-leaf stage (*Pl. viticola* on vines)

| Level of action of R-metalaxyl and racemic metalaxyl | | |
|---|---|---|
| Active ingredient | Dose [mg of a.i./litre] | Foliar infestation [%] |
| R-metalaxyl | 200 | 0 |
| | 60 | 0 |
| | 20 | 0 |
| | 6 | 0 |
| | 2 | 0 |
| | 0.6 | 0 |
| | 0.2 | 78 |
| | 0.06 | 93 |
| untreated control | | 92 |
| racemic metalaxyl | 200 | 0 |
| | 60 | 0 |
| | 20 | 27 |
| | 6 | 85 |
| | 2 | 80 |
| | 0.6 | 96 |
| | 0.2 | 90 |
| | 0.06 | 92 |

While conventional racemic metalaxyl shows virtually no activity in a concentration range of 6 mg of a.i./liter (or less) and a more clear-cut activity is only discernible at 20 mg of a.i./liter, the activity of enantiomeric R-metalaxyl is approximately 100 times better up to a concentration range of 0.6 mg of a.i./liter.

II Degradation of the active ingredients in the soil

EXAMPLE 1

Degradation Behaviour of Racemic Metalaxyl and R-metalaxyl in Moderately Heavy Soil Two groups of 8 samples each of biologically active soil (silt/loam; loam: 13.9%; silt: 54.3%; sand: 31.8%; organic carbon: 2.1%; pH 7.3; biomass: 65.1 mg microbial carbon per 100 g soil; origin: Les Evouettes, Valais, Switzerland) are treated in parallel with racemic metalaxyl or R-metalaxyl, respectively, in each case in acetonic solution. The rate of application is 0.5 mg/kg of soil sample, which corresponds to a rate of application of 0.5 kg/hectare. The results are evaluated in duplicate after 0, 7, 14 and 21 days.

Results:

TABLE 1

Rate of Degradation of rac. Metalaxyl and R-Metalaxyl in fieldfresh Soil (Silt/loam) under laboratory Conditions

| Time | racemic metalaxyl (% of applied) | | R-metalaxyl (% of applied) | |
|---|---|---|---|---|
| (days) | | mean | | mean |
| 0 | 90.41 | | 93.61 | |
| 0 | 90.36 | 90.39 | 98.94 | 96.28 |
| 7 | 47.28 | | 24.74 | |
| 7 | 45.17 | 46.23 | 25.7 | 25.23 |
| 14 | 35.88 | | 9.07 | |
| 14 | 35.54 | 35.71 | 10.62 | 9.85 |

TABLE 1-continued

Rate of Degradation of rac. Metalaxyl and R-Metalaxyl in fieldfresh Soil (Silt/loam) under laboratory Conditions

| Time | racemic metalaxyl (% of applied) | | R-metalaxyl (% of applied) | |
|---|---|---|---|---|
| (days) | mean | | mean | |
| 21 | 29.34 | | 7.57 | |
| 21 | 29.06 | 29.20 | 7.82 | 7.69 |

The degradation equations are:
Metalaxyl racemate: $C_t = 86.66 * e^{(-0.0644*t)}$
DT-50 = ln2/0.0644; DT-90 = ln10/0.0644
R-metalaxyl: $C_t = 95.9 * e^{(-0.1776*t)}$
DT-50 = ln2/0.01776; DT-90 = ln10/0.1776
The degradation curves are shown in FIG. 1 (Appendix).

They allow the following degradation times to be calculated:

| | racemic metalaxyl | R-metalaxyl |
|---|---|---|
| DT-50:(50% degradation) | 10.8 days | 3.9 days |
| DT-90:(90% degradation) | 35.7 days | 13.0 days |

EXAMPLE 2

Degradation Behaviour of Racemic Metalaxyl and R-metalaxyl in Sandy Soil

Two groups of 16 samples each of biologically active soil (sandy soil; loam: 5.1%; silt: 11.4%; sand: 83.5%; organic carbon: 1.6%; pH 4; biomass: 51 mg microbial carbon/100 g soil; origin: Collombey, Valais, Switzerland) are treated in parallel with racemic metalaxyl or R-metalaxyl, respectively, in each case in acetonic solution. The rate of application is 0.5 mg/kg of soil sample, which corresponds to a rate of application of 0.5 kg/hectare. The results are evaluated in duplicate after 0, 1, 3, 7, 9, 15, 21 and 29 days.
Results:

TABLE 2

Rate of Degradation of rac. Metalaxyl and R-Metalaxyl in fieldfresh Soil (Sand) under laboratory Conditions.

| Time | racemic metalaxyl (% of applied) | | R-metalaxyl (% of applied) | |
|---|---|---|---|---|
| (days) | mean | | mean | |
| 0 | 98.00 | | 100.32 | |
| 0 | 97.56 | 97.78 | 99.72 | 100.02 |
| 1 | 87.75 | | 89.16 | |
| 1 | 87.88 | 87.82 | 90.13 | 89.64 |
| 3 | 80.32 | | 76.96 | |
| 3 | 79.69 | 80.01 | 74.01 | 75.48 |
| 7 | 65.41 | | 52.59 | |
| 7 | 64.60 | 65.01 | 52.59 | 52.59 |
| 9 | 55.84 | | 47.22 | |
| 9 | 56.68 | 56.26 | 46.45 | 46.84 |
| 15 | 43.49 | | 24.77 | |
| 15 | 41.58 | 42.54 | 29.89 | 27.33 |
| 21 | 30.77 | | 17.12 | |

TABLE 2-continued

Rate of Degradation of rac. Metalaxyl and R-Metalaxyl in fieldfresh Soil (Sand) under laboratory Conditions.

| Time | racemic metalaxyl (% of applied) | | R-metalaxyl (% of applied) | |
|---|---|---|---|---|
| (days) | mean | | mean | |
| 21 | 33.21 | 31.99 | 17.05 | 17.09 |
| 29 | 28.70 | | 8.82 | |
| 29 | 28.28 | 28.49 | 8.62 | 8.72 |

Degradation equations
rac. Metalaxyl: $Ct = 93.67 * e^{(-0.05006*t)}$; DT-50 = ln 2/0.05006; DT-90 = ln 10/0.5006
R-Metalaxyl: $Ct = 98.53 * e^{(-0.08548*t)}$; DT-50 = ln 2/0.08548; DT-90 = ln 10/0.08548
The degradation curves are shown in FIG. 2 (Appendix).

They allow the following degradation times to be calculated:

| | racemic metalaxyl | R-metalaxyl |
|---|---|---|
| DT-50:(50% degradation) | 13.9 days | 8.1 days |
| DT-90:(90% degradation) | 46.0 days | 26.9 days |

What we claim is:

1. A fungicidal composition having improved degradation in the soil, on the basis of the Oomycetes controlling fungicide metalaxyl wherein the content of the R-enantiomer in the active ingredient is more than 70% b.w., together with a suitable carrier material therefor.

2. A composition of claim 1, wherein the content of the R-enantiomer in the active ingredient is more than 85% by weight.

3. A composition of claim 2, wherein the content of the R-enantiomer in the active ingredient is more than 92% by weight.

4. A composition of claim 3, wherein the content of the R-enantiomer in the active ingredient is more than 97% by weight.

5. A composition of claim 4, wherein the active ingredient is substantially free from S-enantiomer.

6. A composition of claim 1, wherein the content of the active ingredient in the composition is more than 30% by weight.

7. The compound which is substantially free of the S-enantiomer selected from the group consisting of the compound having the formula:

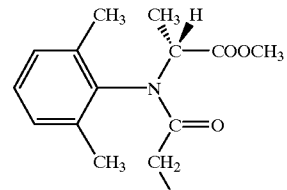

wherein R is $OCH_3$.

* * * * *